(12) United States Patent
Siebels et al.

(10) Patent No.: US 9,371,585 B2
(45) Date of Patent: Jun. 21, 2016

(54) METHOD AND DEVICE FOR PLASMA-TREATING WORKPIECES

(75) Inventors: Sönke Siebels, Hamburg (DE); Sebastian Kytzia, Hamburg (DE)

(73) Assignee: KHS CORPOPLAST GMBH, Hamburg (DE)

( * ) Notice: Subject to any disclaimer, the term of this patent is extended or adjusted under 35 U.S.C. 154(b) by 553 days.

(21) Appl. No.: 13/634,138

(22) PCT Filed: Mar. 3, 2011

(86) PCT No.: PCT/DE2011/000234
§ 371 (c)(1),
(2), (4) Date: Sep. 11, 2012

(87) PCT Pub. No.: WO2011/110162
PCT Pub. Date: Sep. 15, 2011

(65) Prior Publication Data
US 2013/0004682 A1 Jan. 3, 2013

(30) Foreign Application Priority Data

Mar. 12, 2010 (DE) .................. 10 2010 012 501

(51) Int. Cl.
| | |
|---|---|
| C23C 16/00 | (2006.01) |
| C23C 16/52 | (2006.01) |
| C23C 16/04 | (2006.01) |
| C23C 16/511 | (2006.01) |
| G01J 3/02 | (2006.01) |
| G01J 3/443 | (2006.01) |
| G01N 21/68 | (2006.01) |
| H01J 37/32 | (2006.01) |

(52) U.S. Cl.
CPC ............ *C23C 16/52* (2013.01); *C23C 16/045* (2013.01); *C23C 16/511* (2013.01); *G01J 3/02* (2013.01); *G01J 3/0218* (2013.01); *G01J 3/443* (2013.01); *G01N 21/68* (2013.01); *H01J 37/32192* (2013.01); *H01J 37/32779* (2013.01); *H01J 37/32935* (2013.01)

(58) Field of Classification Search
CPC ..................................................... C23C 16/511
USPC .................................................. 427/230–239
See application file for complete search history.

(56) References Cited

U.S. PATENT DOCUMENTS

| | | | |
|---|---|---|---|
| 6,117,243 A | 9/2000 | Walther | |
| 6,328,805 B1 | 12/2001 | Rius | |
| 6,565,791 B1 | 5/2003 | Laurent | |
| 6,818,068 B1 | 11/2004 | Guiffant et al. | |

(Continued)

FOREIGN PATENT DOCUMENTS

| | | |
|---|---|---|
| DE | 102004020185 | 11/2005 |
| DE | 102004042431 | 3/2006 |

(Continued)

*Primary Examiner* — Elizabeth Burkhart
(74) *Attorney, Agent, or Firm* — Lucas & Mercanti, LLP; Klaus P. Stoffel (57) ABSTRACT

The method and device are used to plasma-treat workpieces. The workpiece is inserted into a chamber of a treatment station that can be at least partially evacuated. The plasma chamber is bounded by a chamber bottom, a chamber cover, and a lateral chamber wall. The method process is optically monitored at least at times. In the optical monitoring, spectral lines of the radiation of the plasma above 500 nanometers are evaluated. Preferably, the evaluation is performed for frequencies above 700 nanometers.

7 Claims, 9 Drawing Sheets

(56) References Cited

U.S. PATENT DOCUMENTS

| | | |
|---|---|---|
| 7,947,337 B2 | 5/2011 | Kuepper et al. |
| 2005/0118365 A1 | 6/2005 | Miyazaki et al. |
| 2006/0051520 A1* | 3/2006 | Behle et al. ............... 427/569 |
| 2008/0124488 A1* | 5/2008 | Kuepper et al. ........... 427/569 |
| 2008/0292781 A1* | 11/2008 | Rius et al. .................... 427/8 |

FOREIGN PATENT DOCUMENTS

| | | |
|---|---|---|
| DE | 102006053366 A | 5/2008 |
| DE | 102008016923 A | 10/2009 |
| EP | 1010773 | 6/2000 |
| EP | 1500600 | 1/2005 |
| EP | 1630848 | 3/2006 |
| EP | 1948846 B1 | 5/2009 |
| JP | 2005083835 A | 3/2005 |
| WO | 9522413 | 8/1995 |
| WO | 9917334 | 4/1999 |
| WO | 0058631 | 10/2000 |
| WO | 0131680 | 5/2001 |

* cited by examiner

METHOD AND DEVICE FOR PLASMA-TREATING WORKPIECES

The present application is a 371 of International application PCT/DE2011/000234, filed Mar. 3, 2011, which claims priority of DE 10 2010 012 501.6, filed Mar. 12, 2010, the priority of these applications is hereby claimed and these applications are incorporated herein by reference.

BACKGROUND OF THE INVENTION

The invention relates to a method for plasma treatment of workpieces in which the workpiece is placed in a plasma chamber, and in which, subsequently, under the influence of negative pressure after the ignition of plasma, a coating is precipitated on the workpiece, and in which the process sequence is optically monitored at least temporarily.

Moreover, the invention also relates to a device for plasma treatment of workpieces which has at least one evacuatable plasma chamber for receiving the workpieces, and in which the plasma chamber is arranged in the area of a treatment station, and in which the plasma chamber is defined by a chamber floor, a chamber cover as well as a lateral chamber wall, and in which the plasma chamber is coupled to a device for the optimum monitoring of a process sequence.

Such methods and devices are used, for example, for providing synthetic materials with surface coatings. In particular, also already known are devices of this type for coating inner and outer surfaces of containers which are intended for packaging liquids. Moreover, devices for plasma sterilization are known.

PCT/WO 95/22413 describes a plasma chamber for the internal coating of bottles of PET. The bottles to be coated are lifted through a movable bottom into a plasma chamber and are connected to an adapter in the area of a bottle opening. An evacuation of the bottle interior can be effected through the adapter. Moreover, a hollow gas lance is introduced into the interior of the bottles in order to supply process gas. An ignition of the plasma takes place with the use of a microwave.

It is also known from this publication to arrange a plurality of plasma chambers on a rotating wheel. This supports a high production rate of bottles per unit of time.

In EP-OS 10 10 773 a supply device is explained for evacuating the interior of the bottle and supplying process gas. PCT-WO 01/31680 describes a plasma chamber into which the bottles are inserted by a movable cover which previously had been connected to the mouth portion of the bottles.

PCT-WO 00/58631 also already shows the arrangement of plasma stations on a rotating wheel and describes for such an arrangement an assignment of negative pressure pumps and plasma stations in groups, in order to support a favorable evacuation of the chambers as well as the inner spaces of the bottles. Moreover, the coating of several containers in a common plasma station or a common cavity is mentioned.

Another arrangement for carrying out an internal coating of bottles is described in PCT-WO 99/17334. In this case, especially an arrangement of a microwave generator above the plasma chamber, as well as a vacuum and operation medium through a bottom of the plasma chamber, is described.

In DE 10 2004 020 185 A1 a gas lance is already described which can be moved into the interior of a preform to be coated and for supplying process gas. The gas lance can be positioned in the longitudinal direction of the container.

In a predominant number of the known devices, container layers of silicone oxides produced by the plasma having the general chemical formula $SiO_x$ are used for improving the barrier properties of the thermoplastic material. Such barrier layers prevent a penetration of oxygen into the packaged liquids, as well as a discharge of carbon dioxide in the case of $CO_2$ containing liquids.

Because of the chemical elements contained in the plasma, the plasma has characteristic spectral lines. Therefore, an optical monitoring for carrying out a plasma coating is already described in U.S. Pat. No. 6,117,243. In this case, the evaluation of the radiation emission is carried out within the range of a wave length of 425 nanometers.

EP 1 948 846 explains another method for monitoring a plasma coating. In that case, an evaluation in a spectral range of 800 nanometers to 950 nanometers takes place. An evaluation of a difference between signals of a first band width as the reference and the signals of a second band width takes place.

The previously known methods and devices are not yet sufficiently suitable for making available a process monitoring which is reliable, on the one hand, as well as a process monitoring which is robust with respect to changing border conditions.

SUMMARY OF THE INVENTION

Therefore, it is the object of the invention to improve a process of the above-mentioned type in such a way that reliable process monitoring is reinforced.

In accordance with the invention, this object is met in that, during optical monitoring, wave lengths of the emission radiation of the plasma above 500 nanometers are evaluated.

A further object of the present invention is to make available a device of the above-mentioned type in such a way that a reliable process monitoring is achieved.

This object is met in accordance with the invention in that the device for optical monitoring is constructed for evaluating spectral lines emitted by the plasma above 500 nanometers.

The method according to the invention and the device according to the invention are particularly suitable for monitoring the sequence of a coating process for bottles of synthetic material. To this end, especially an inner coating of these bottles with a layer of $SiO_x$ takes place, wherein the adherence of the layer of $SiO_x$ on the synthetic material can be improved by an intermediate layer which is constructed as an adhesion promoter. The coating process is preferably carried out as a PICVD plasma process (plasma impulse chemical vapor deposition). In such a method, the plasma is ignited by means of an impulse of a microwave. The impulses can be controlled, with respect to their pulse width, the pulse spacing as well as the pulse height.

By using optical monitoring, it is possible to monitor the gas composition of the plasma as well as the microwave power which has been introduced into the plasma.

This entry of microwave power is in direct dependence on the adjustment of the microwave system as well as of the energy introduced into the magnetron. Therefore, monitoring of the energy introduced into the magnetron is necessary for being able to evaluate the total system.

In accordance with the prior art, optical monitoring of a coating process in the range of visible light has the advantage that the coated workpieces can be distinguished by color and that the transmission properties with respect to visible light cannot be significantly influenced as a result.

Therefore, in accordance with the invention, an optimum emission spectroscopy takes place above 500 nanometers.

Preferably, it is contemplated to evaluate wave lengths above 600 nanometers.

In particular, it has also been found advantageous to evaluate spectral lines above 700 nanometers.

A particularly safe evaluation can be obtained by considering two different wave lengths.

For achieving a simple construction of the device, at least a portion of the monitored emission radiation of the plasma is transmitted by at least one light wave conductor.

Also, it has been found particularly advantageous for process monitoring that the light wave conductor is coupled to at least one photo element whose signal is amplified in a local vicinity to the photo element.

A particularly good sensitivity to problems is achieved by integrating at least a portion of the signal pattern, determined by optical monitoring, over at least a predeterminable period of time.

DETAILED DESCRIPTION OF THE INVENTION

Figure 1:
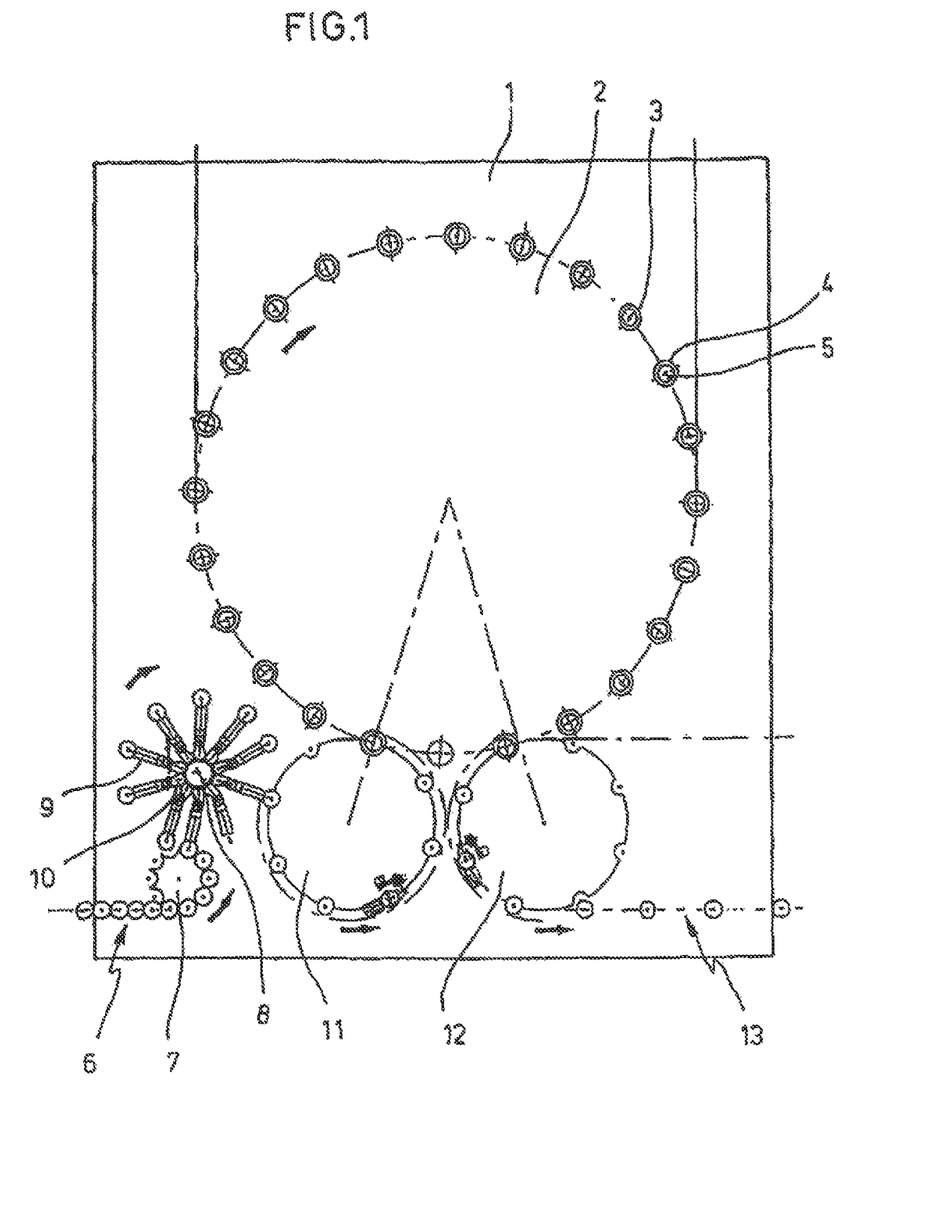
FIG. 1 shows a principle sketch of a plurality of plasma chambers which are arranged on a rotating plasma wheel and in which the plasma wheel is coupled to input and output wheels.

The illustration of FIG. 1 shows a plasma module 1, which is provided with a rotating plasma wheel 2. Along a circumference of the plasma wheel 2, a plurality of plasma stations 3 are arranged. The plasma stations 3 are provided with cavities 4, or plasma chambers 17, for receiving the workpieces 5 to be treated.

The workpieces 5 to be treated are supplied to the plasma module 1 in the area of an input 6, and are further conveyed to a transfer wheel 8 through a separating wheel 7, wherein the transfer wheel 8 is equipped with positionable support arms 9. The support arms 9 are arranged so as to be pivotable relative to a base 10 of the transfer wheel 8, so that a change of the distance of the workpieces 5 relative to each other can be carried out. This causes a transfer of the workpieces 5 from the transfer wheel 8 to an input wheel 11 with a spacing of the workpieces 5 which is increased relative to the separating wheel 7. The input wheel 11 transfers the workpieces 5 to be treated to the plasma wheel 2. After a treatment has been carried out, all treated workpieces 5 are removed from an output wheel 12 from the area of the plasma wheel 2 and are transferred into the area of an output section 13.

Figure 2:
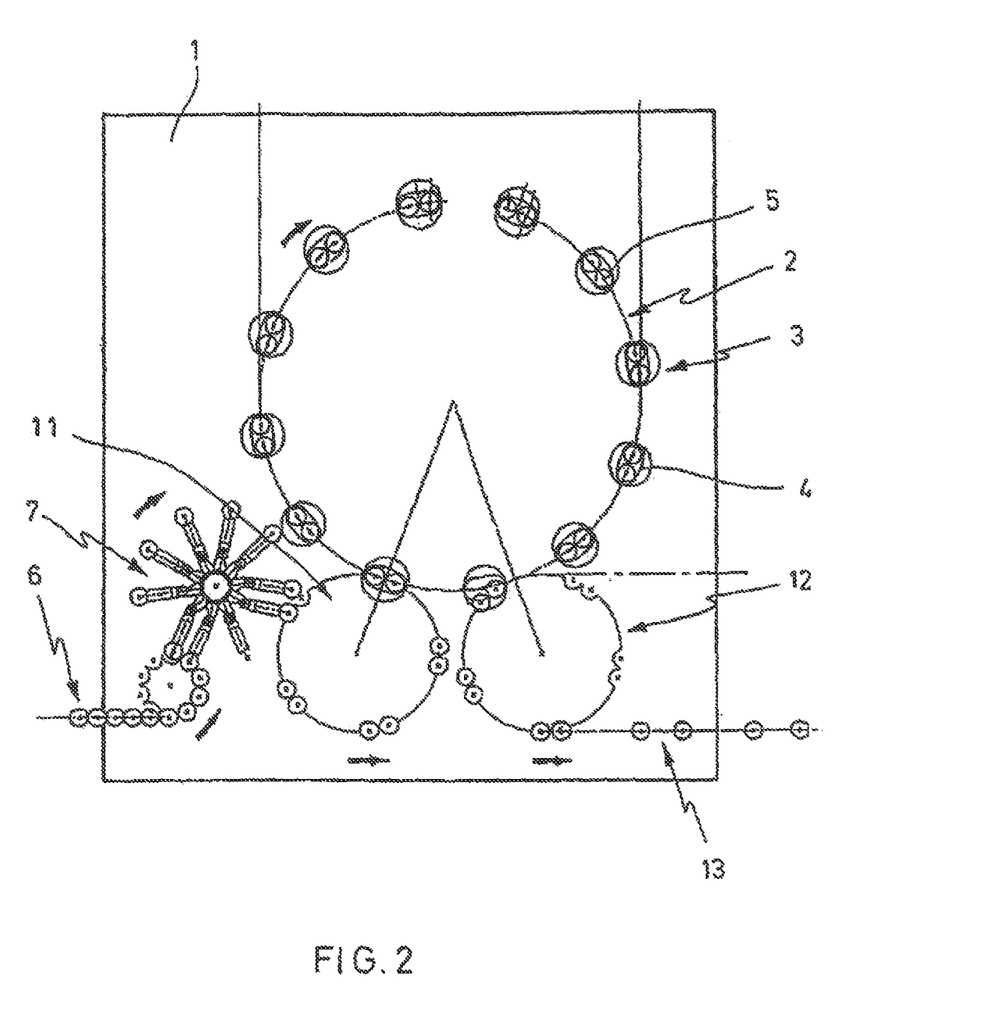
FIG. 2 shows an arrangement, similar to FIG. 1, in which the plasma stations are each equipped with two plasma chambers.

In the embodiment according to FIG. 2, the plasma stations 3 are each equipped with two cavities 4 or plasma chambers 17. Accordingly, always two workpieces 5 can be treated simultaneously. Basically, it is also possible in this connection to construct the cavities 4 so as to be completely separate from each other. However, it is essentially also possible to delimit in a common cavity space only partial areas relative to each other in such a way that an optimum feeding of all workpieces 5 is ensured. In particular, it is intended to delimit the partial cavities relative to each other, at least through separate microwave couplings.

Figure 3:
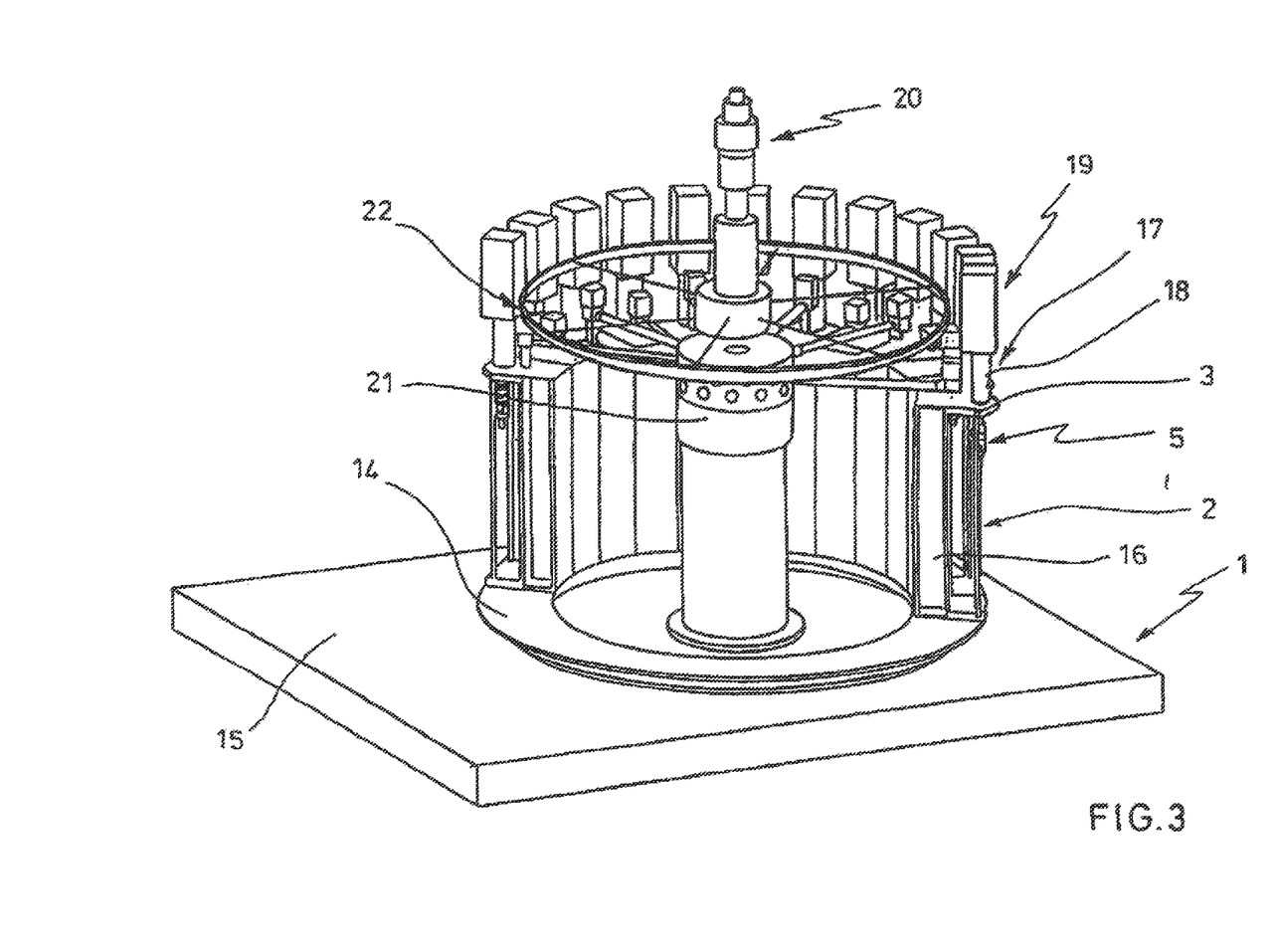
FIG. 3 is a perspective illustration of a plasma wheel with a plurality of plasma chambers.

FIG. 3 is a perspective illustration of a plasma module 1 with a partially built-up plasma wheel 2. The plasma stations 3 are arranged on a support ring 14 which is constructed as part of a rotary connection and is supported in the area of a machine base 15. The plasma stations 3 each have a station frame 16 which support the plasma chambers 17. The plasma chambers 17 include cylindrical chamber walls 18 as well as microwave generators 19.

In a center of the plasma wheel 2, a rotary distributor 20 is arranged through which the plasma stations 3 are supplied with drive means as well as energy. For distributing the operating means, particularly ring-shaped lines 21 can be used.

The workpieces 5 to be treated are illustrated underneath the cylindrically shaped chamber walls 18. Bottom parts in each of the plasma chambers 17 are not illustrated for simplicity's sake.

Figure 4:
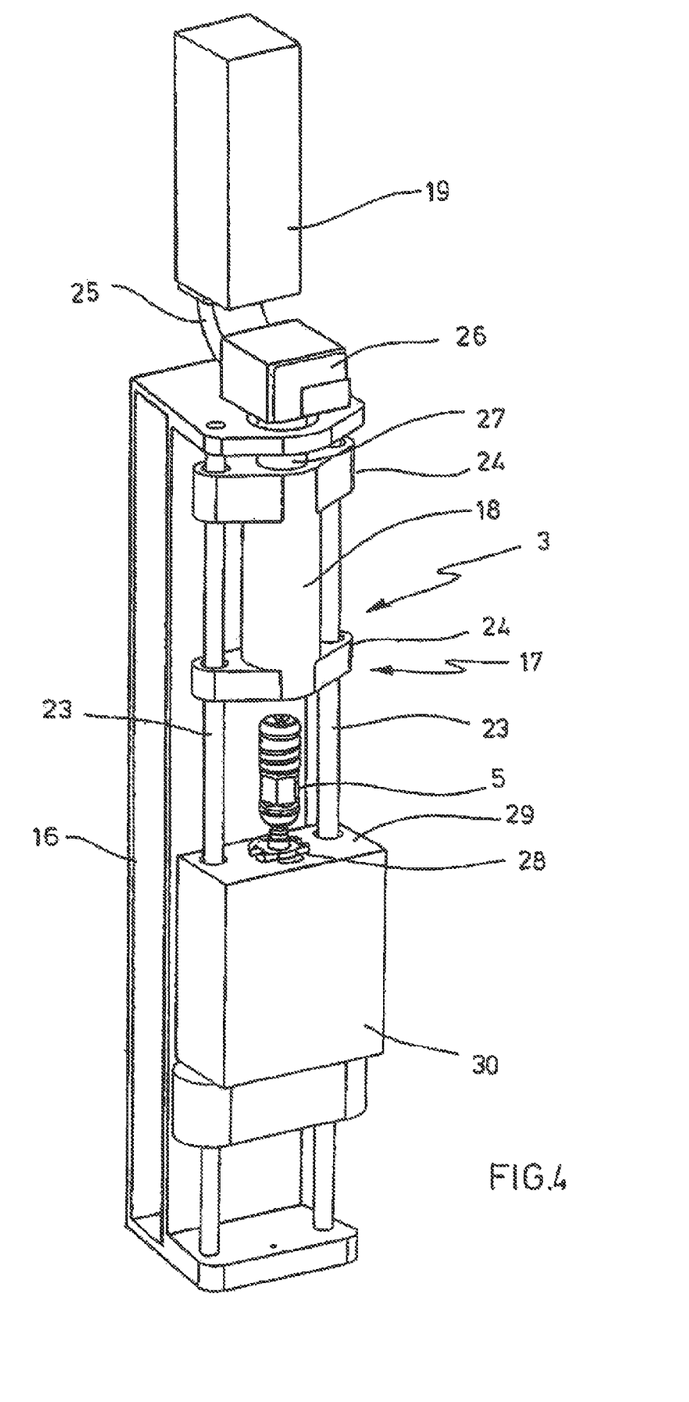
FIG. 4 is a perspective illustration of a plasma station with one cavity.

FIG. 4 shows a plasma station 3 in a perspective view. It can be seen that the station frame 16 is provided with guide rods on which is guided a carriage 24 for supporting the cylindrical chamber wall 18. FIG. 4 shows the carriage 24 with chamber wall 18 in an elevated state, so that the workpiece 5 is released.

The microwave generator 19 is arranged in the upper portion of the plasma station 3. The microwave generator 19 is connected through a deflection means 25 and an adaptor 26 to a coupling duct 27 which leads into the plasma chamber 17. The microwave generator 19 can basically be coupled immediately in the area of the chamber cover 31, as well as through a spacer element at a predeterminable distance from the chamber cover 31 and, thus, in a larger neighboring area of the chamber cover 31. The adaptor 26 has the function of a transfer element and the coupling duct 27 is constructed as a coaxial conductor. A quartz glass window is arranged in the area of an opening of the coupling duct 27 in the chamber cover 31. The deflection means 25 is constructed as a hollow conductor.

The workpiece 5 is positioned in the area of a duct chamber by a holding element 28 arranged in the area of a chamber bottom 29. The chamber bottom 29 is constructed as part of a chamber base 30. For facilitating an adjustment, it is possible to fix the chamber base 30 in the area of the guide rods 23. Another variation resides in fastening the chamber base 30 directly at the station frame 16. In such an arrangement, it is also possible to construct the guide rods 23 of two parts in the vertical direction.

Figure 5:
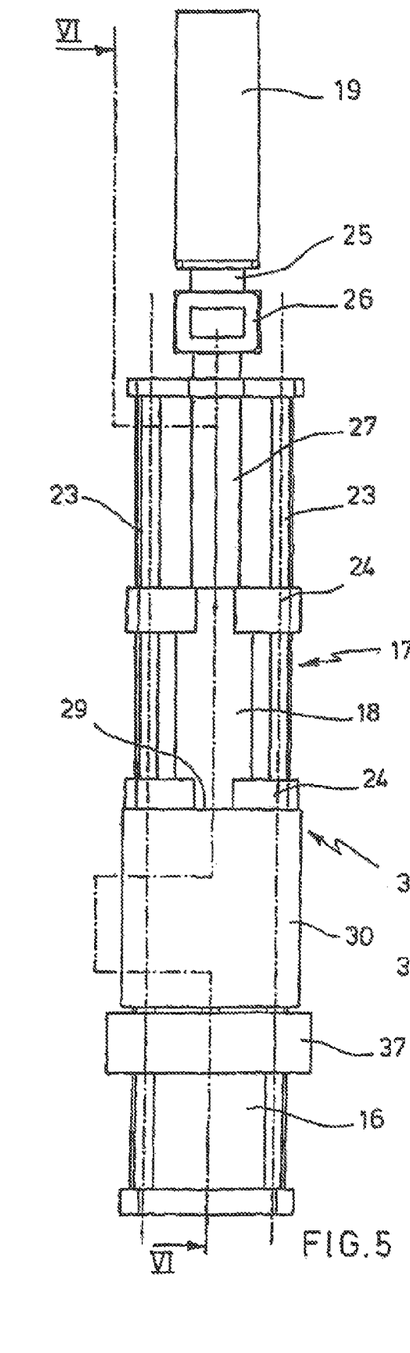
FIG. 5 is a front view of the device according to FIG. 4 with closed plasma chamber.

FIG. 5 shows a front view of the plasma station 3 in accordance with FIG. 3 in a closed state of the plasma chamber 17. The carriage 24 with the cylindrically shaped chamber wall 18 is lowered relative to the positioning in FIG. 4, so that the chamber wall 18 is placed against the chamber bottom 29. The plasma coating can be carried out in this state of positioning.

Figure 6:
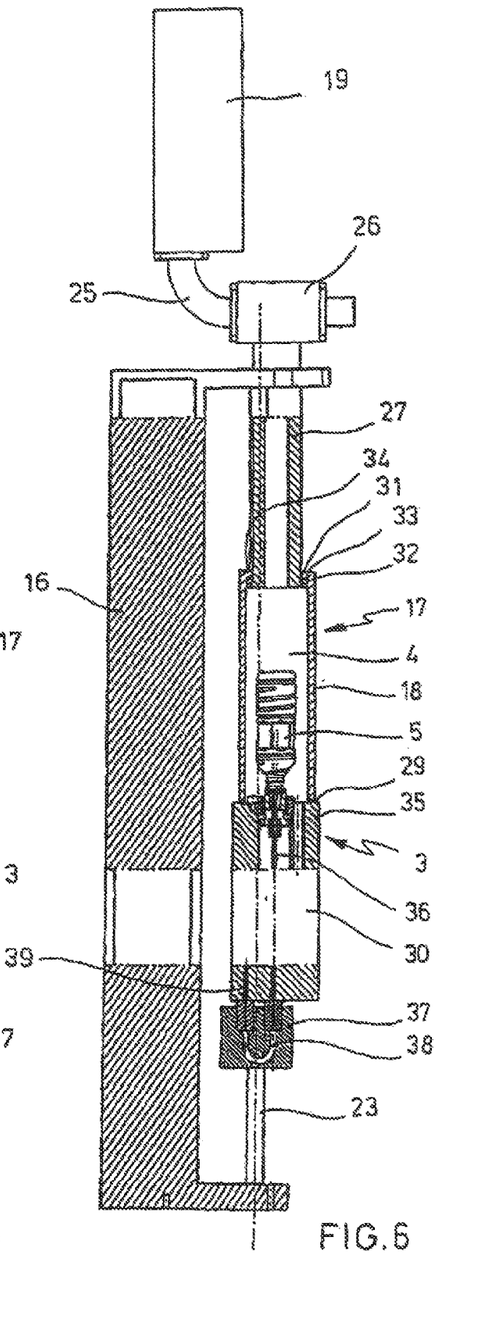
FIG. 6 is a cross sectional view along sectional line VI-VI in FIG. 5.

FIG. 6 shows, in a vertical sectional view, the arrangement according to FIG. 5. It can be especially seen that the coupling duct 27 opens into a chamber cover 31 which includes a laterally projecting flange 32. Arranged in the area of the flange 32 is a sealing unit 33 which is acted upon by an inner flange 34 of the chamber wall 18. In a lowered state of the chamber wall 18, this results in a sealing action of the chamber wall 18 relative to the chamber cover 31. Another sealing unit 35 is arranged in a lower part of the chamber wall 18 to ensure, also at this location, a sealing action relative to the chamber bottom 29.

In the positioning illustrated in FIG. 6, the chamber wall 18 surrounds the cavity 4, so that an interior space of the cavity 4, as well as an interior space of the workpiece 5, can be evacuated. For supporting a supply of process gas, a hollow gas lance 36 is arranged in the area of the chamber bottom 30, wherein the gas lance can be moved into the interior space of the workpiece 5. For carrying out positioning of the gas lance 36, the gas lance is held by a lance carriage 37 which is positionable along the guide rods 23. A process gas channel 38 extends within the lance carriage 37, wherein, in the raised position illustrated in FIG. 6, the process gas channel 38 is coupled to a gas connection 39 of the chamber base 30. As a result of this configuration, hose-like connecting elements at the lance carriage 37 are avoided.

As an alternative to the above explained construction, it is also possible in accordance with the invention, to introduce the workpiece 5 into a plasma chamber 17 which is arranged so as to be immovable relative to the assigned support structure. As another alternative to the illustrated coating of the workpieces 5 with their openings directed downwardly in the vertical direction, a coating of the workpieces with their openings directed upwardly in the vertical direction is possible. In particular, it is contemplated to carry out coating of bottle shaped workpieces 5. Such bottles are also preferably constructed of a thermoplastic material. Preferably, the use of PET or PP is contemplated. In accordance with another preferred embodiment, the coated bottles are serving to receive beverages.

In the following, a typical treatment procedure will be explained in connection with an example of a coating procedure and is carried out in such a way that, initially, the workpiece 5 is transported to the plasma wheel 2 with the use of an input wheel 11 and the insertion of the workpiece 5 into the plasma station 3 in an upwardly pushed state of the sleeve-like chamber wall 18 takes place.

After the conclusion of the insertion procedure, the chamber wall 18 is lowered into its sealed position and, offset with respect to time, a displacement of the holding element 28 takes place, so that a separation of the inner space of the workpiece 5 relative to the interior space of the cavity 4 is created. Subsequently, the gas lance 36 is moved into the interior space of the workpiece 5. It is also possible to move the gas lance 36 into the interior of the workpiece 5 already synchronously with the beginning of the lowering of the cavity 4 into the interior space of the workpiece 5. This is followed by an evacuation of the cavity 4 and of the interior space of the workpiece 5, either simultaneously or offset with respect to time. After the interior space of the cavity 4 has been sufficiently evacuated, the pressure in the interior space of the workpiece 5 is lowered further. Moreover, it is also contemplated to carry out the positioning movement of the gas lance 36 at least partially already parallel with the positioning of the chamber wall 18.

After reaching a sufficiently low negative pressure, the process gas is conducted into the interior of the workpiece 5 and the plasma is ignited by means of the microwave generator 19. In particular, it is contemplated to separate out, by means of the plasma, an adhesion promoter to an inner surface of the workpiece 5 as well as the actual barrier layer of silicon oxides.

After the conclusion of the coating procedure, the plasma chamber 17, as well as the interior space of the workpiece 5, are ventilated. After the ambient pressure within the cavity 4 and the interior space of the workpiece 5 has been reached, the chamber wall 18 is once again raised and the gas lance 36 is once again removed from the interior space of the workpiece 5. A removal of the coated workpiece 5, as well as the introduction of a new workpiece 5 to be coated, can now be carried out.

Positioning of the chamber wall 18, of the sealing element 28 and/or of the gas lance 36 can be carried out with the use of different drive units. Basically, the use of pneumatic drives and/or electric drives, in particular in the form of an embodiment as a linear motor, is conceivable. In particular, however, it is contemplated to realize, for supporting an exact coordination of movements, a cam control with a rotation of the plasma wheel 2. The cam control can be carried out, for example, in such a way that control curves are arranged along a circumference of the plasma wheel 2, wherein cam rollers are guided along the control curves. The cam rollers are coupled to the structural elements to be positioned respectively.

Figure 7:
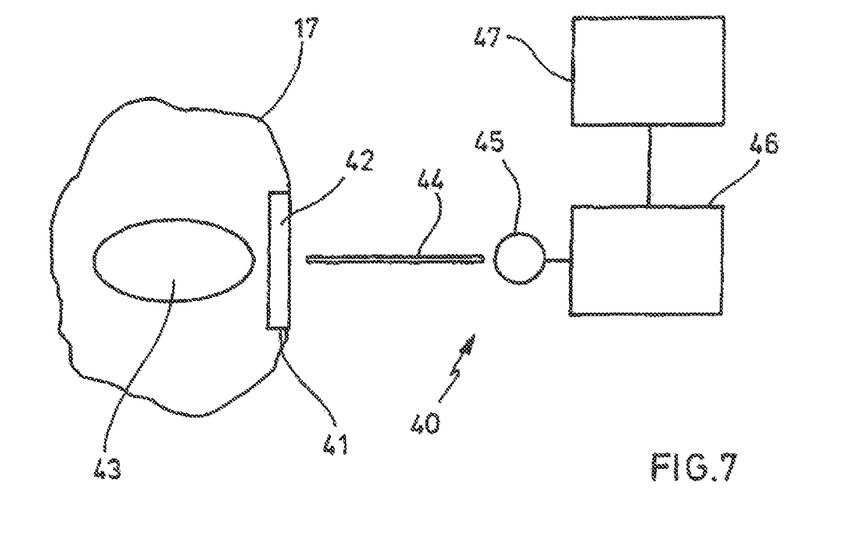
FIG. 7 shows an optical connection of a quartz glass disc, facing the process to be monitored, to a photo element with the use of a cable for conducting light waves.

FIG. 7 shows a schematic illustration of a device 40 for optically monitoring a coating procedure. The plasma chamber 17 provided with a window 41 is illustrated schematically. A quartz glass disc 42 is placed in the window 41. Plasma 43 is schematically illustrated within the plasma chamber 17.

Starting from the quartz glass disc 42, a light wave conductor extends to a photo element 45. The photo element 45 is directly connected to an amplifying step 52 which is typically coupled directly to an analog/digital converter 46. The analog/digital converter 46 is connected to an evaluating unit 47.

The structural elements 45, 52 46, 47 are thus arranged at a distance from the plasma chamber 17 and are located outside of an immediate influence of the microwave system. The photo element 45 is coupled directly to an amplifying step in order to achieve a low ratio of signal components to noise components. Typical reinforcement factors are in the range of $10^5$ to $10^9$. Preferably, a dark current balance is realized in the area of the amplifier for facilitating a compensation of the thermal behavior of the photo diode and of the amplifying stage. Moreover, an amplifying circuit is implemented. This makes it possible to make available a respectively optimum amplification for different light intensities. The output signal of the amplifier is then supplied to the analog/digital converter 46. The direct coupling of the photo element 45 and the amplifier can be realized, for example, by an arrangement in a common electronic structural group, on a common plate, or on a common semi-conductor chip.

In the area of the evaluation unit 47, it is preferably provided to integrate the signal of the analog/digital converter 46 over a predetermined period of time. The respectively scanned values can be supplied to intermediate storage in order to support a representation of the signal patterns over time.

Figure 8:
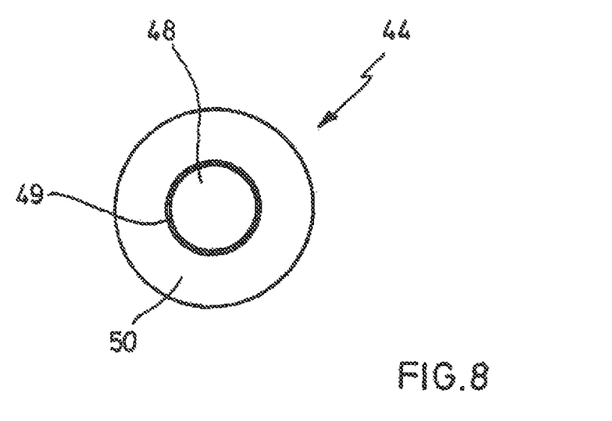
FIG. 8 is a cross sectional view, on a larger scale, through the cable for conducting light waves.

FIG. 8 shows an enlarged cross sectional view of the light wave conductor 44. The light wave conductor has an optical core 48, an optical casing 49 as well as an outer sleeve 50. The core 48 typically has a diameter of about 400 to 600 micrometers. As material for the optical casing 4, PMMA can be used. The use of ETFE for the casing 50 has been found useful.

A typical damping of the light wave conductor 44 in a wave length to be transmitted is about 850 nanometers, at most 8 db/km. The factor NA (Numerical Aperture) is about 0.37. Quartz glass is used as the material for the optical core 48.

Figure 9:
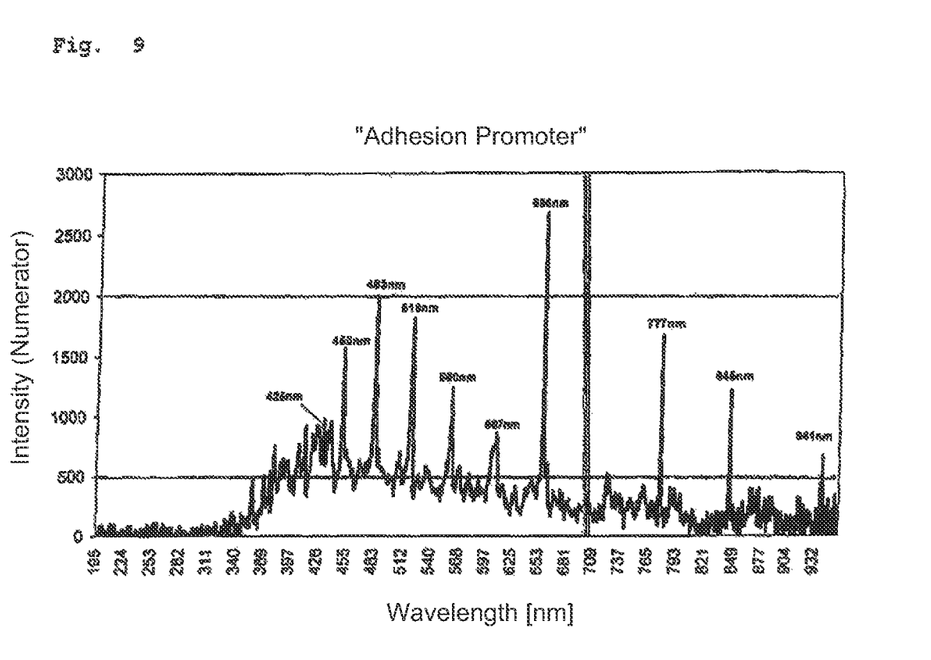
FIG. 9 shows a typical emission spectrum of plasma for SiOx coating of PET bottles with the application of an adhesive layer.

FIG. 9 shows a typical transmission pattern for carrying out an inner coating of PET bottles. In this connection, the process step of applying an adhesive layer between the PET material and the layer of SiOx is carried out. In a range above 700 nanometers, three characteristic spectral lines are obtained. These spectral lines are at 777 nanometers, 845 nanometers and 927 nanometers. Monitoring at least two of these spectral lines, preferably all three spectral lines, has been found particularly advantageous for process monitoring and possibly process control.

Figure 10:
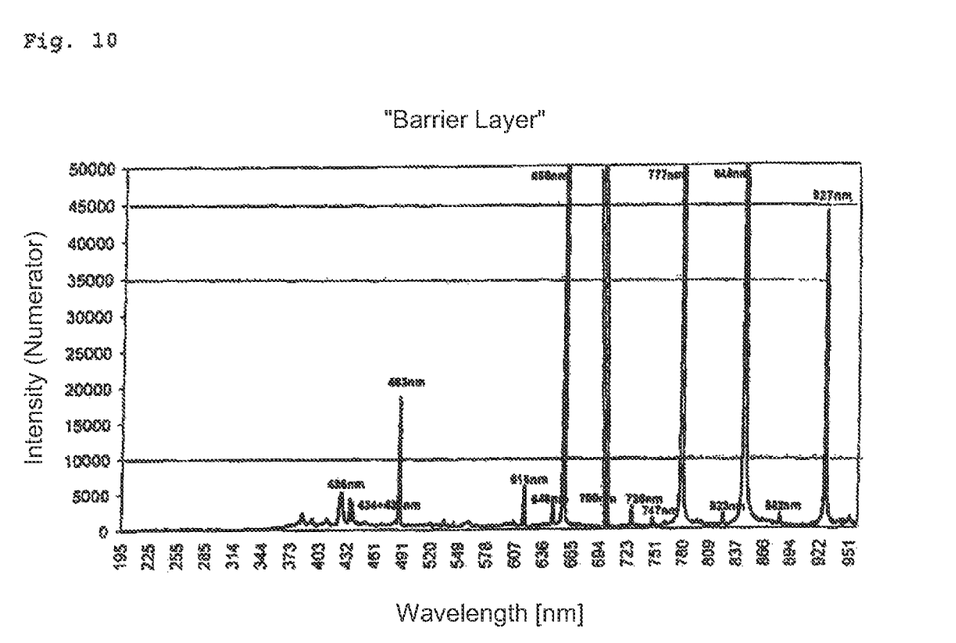
FIG. 10 shows an emission spectrum, similar to FIG. 9, for applying a barrier layer.

FIG. 10 shows a comparable pattern of spectral lines when the SiOx layer is applied. Also in this case, the three characteristic spectral lines mentioned above are developed to a significant extent.

Figure 11:
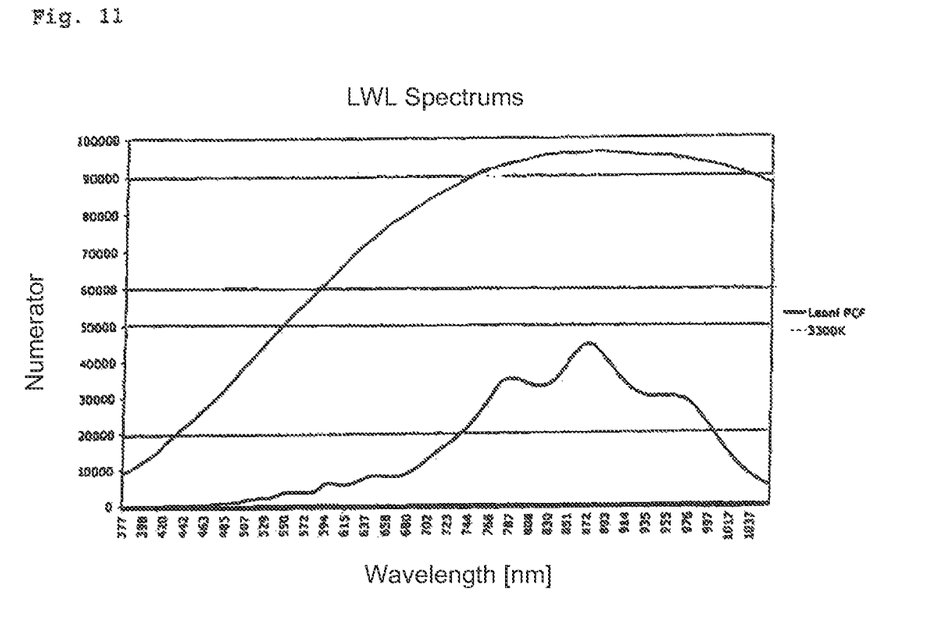
FIG. 11 is an illustration of the transmission characteristics of the light wave conductor used.

FIG. 11 shows the typical spectral range for the preferred light wave conductor. The light wave conductor explained above in more detail corresponds to the pattern 51.

In FIGS. 9 to 11, the respective intensities are shown in counts over the wave length in nanometers.

The light wave conductor according to FIG. 7 has two essential functions. In accordance with a first function, the light wave conductor 44 picks up, through its numerical aperture, the scattered light generated by the plasma 43. As a result, a special collecting lens is not required. The second function of the light wave conductor resides in its property as spectral filter. Because of the spectral behavior illustrated in FIG. 11, different wave lengths (spectral lines) are transmitted with different damping by the light wave conductor 44. The light wave conductor with the pattern 51 in FIG. 11 has an optimized property for the transmission of the spectral lines according to FIG. 9 and FIG. 10.

An inexpensive photo diode having a spectral sensitivity in a range of 700 nanometers to 1,000 nanometers can be used as the photo element 45. Basically, it would also be possible to use photo resistors or photo transistors as photo elements 45. However, photo diodes have a very low inertia.

As already mentioned, an integration of the measured signal patterns is carried out in the area of the evaluation unit 47. The resulting area contents describe the energy contained in the signal. The integration combines a high sensitivity with a high accuracy.

Therefore, the signal transmission through the light wave conductor 44, the selective transmission of wave lengths above 700 nanometers by the optical properties of the light wave conductor 44, the signal amplification carried out in close local vicinity to the photo element 45, the switchable signal amplification, and the integration of signal patterns in the area of the evaluation unit 47, are to be considered the essential components for process monitoring according to the invention. Particularly advantageous is the realization of all five of the above mentioned properties in combination with each other; however, each individual property can also be realized by itself or in combination with only one or with two or three of the additional properties.

With respect to the integration, it is particularly contemplated, not only to integrate the signal of an individual spectral line, but also to integrate all intensities in a predeterminable spectral range, for example, from 700 nanometers to 1,000 nanometers. The resulting area is compared to a reference area and upper and lower limits are to be observed in the case of deviations.

The oxygen line in the spectral range is especially significant for process monitoring.

The invention claimed is:

1. A method for plasma treatment of a workpiece, comprising the steps of: placing the workpiece into a plasma chamber; subsequently, under influence of a negative pressure, precipitating a coating onto the workpiece after ignition of a plasma; and at least temporarily optically monitoring a process sequence, including, during the optical monitoring, evaluating wave lengths of radiation of the plasma above 500 nanometers, transmitting at least a portion of emission radiation of the plasma through at least one light wave conductor to an optical monitor, and integrating the transmitted signal pattern determined by optical monitoring over at least a predeterminable period of time, wherein the wavelengths have wavelength range defined by transmission characteristics of the at least one light wave conductor, including integrating all intensities in a spectral range of 700 to 1000 nanometers.

2. The method according to claim 1, including evaluating wavelengths of radiation of the plasma above 600 nanometers.

3. The method according to claim 1, including evaluating wavelengths of radiation of the plasma above 700 nanometers.

4. The method according to claim 1, including evaluating at least two different spectral lines.

5. The method according to claim 1, including coupling the light wave conductor to at least one photo element whose signal is amplified in a local vicinity to the photo element.

6. The method according to claim 1, including integrating a modulated current/voltage signal pattern issued by a microwave generator, and corresponding to an energy input into a magnetron, over at least a predeterminable period of time.

7. The method according to claim 6, including using the integration value as reference in correlation to an integration value of the optical monitoring.

* * * * *